United States Patent [19]

Jandacek et al.

[11] Patent Number: 4,753,963

[45] Date of Patent: Jun. 28, 1988

[54] NUTRITIONAL FAT SUITABLE FOR ENTERAL AND PARENTERAL PRODUCTS

[75] Inventors: Ronald J. Jandacek, Cincinnati, Ohio; Robert A. Volpenhein, West Harrison, Ind.

[73] Assignee: The Procter & Gamble Company, Cincinnati, Ohio

[21] Appl. No.: 780,473

[22] Filed: Sep. 26, 1985

[51] Int. Cl.$^4$ .................. A61K 31/23; A23D 5/00
[52] U.S. Cl. ...................... 514/552; 514/558; 514/560; 426/607
[58] Field of Search ............ 514/552, 558, 560; 260/410.7; 426/607

[56] References Cited

U.S. PATENT DOCUMENTS 3,450,819  6/1969  Babayan et al. ............ 514/557
4,526,793  7/1985  Ingenbleek et al. ......... 426/72
4,528,197  7/1985  Blackburn ................. 514/552
4,607,052  8/1986  Mendy et al. .............. 260/410.7

FOREIGN PATENT DOCUMENTS 2515174  4/1983  France .

OTHER PUBLICATIONS

Babayan, "Medium Chain Length Fatty Acid Esters and Their Medical and Nutritional Applications", *J. Am. Oil Chem. Soc.*, vol. 58 (1981), pp. 49A–51A.
Bach et al., "Medium-Chain Triglycerides: an update", *Am. J. Clin. Nutr.*, vol. 36 (1982), pp. 950–962.
Mok et al., "Structured Medium-Chain and Long-Chain Triglyceride Emulsions are Superior to Physical Mixtures in Sparing Body Protein in the Burned Rat", *Metabolism*, vol. 33 (Oct. 1984), pp. 910–915.
Maiz et al., "Protein Metabolism During Total Parenteral Nutrition (TPN) in Injured Rats Using Medium-Chain Triglycerides," *Metabolism*, vol. 33 (Oct. 1984), pp. 901–909.
Stein et al., "Comparison of Glucose, LCT, and LCT plus MCT as Calorie Sources for Parenterally Nourished Rats," *Am. J. Physiol.*, vol. 246 (1984), pp. E277–E287.
*Chem. Abs.* 74:1665k.
*Chem. Abs.* 100: 173597m.

Primary Examiner—J. R. Brown
Assistant Examiner—Jacqueline M. Stone
Attorney, Agent, or Firm—Eric W. Guttag; Gretchen R. Babcock; Steven J. Goldstein

[57] ABSTRACT

A nutritonal fat suitable for enteral and parenteral products is disclosed. This fat consists essentially of from about 50 to 100% by weight triglycerides having the formula:

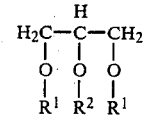

wherein each $R^1$ group is selected from n-heptanoyl, n-octanoyl, n-nonanoyl, n-decanoyl and n-undecanoyl groups; and the $R^2$ groups comprise from 0 to about 90% saturated acyl groups selected from n-heptanoyl, n-octanoyl, n-nonanoyl, n-decanoyl, n-undecanoyl, lauroyl, myristoyl, palmitoyl, stearoyl and mixtures thereof; from 0 to about 90% oleoyl groups; from about 10 to 100% linoleoyl groups; and from 0 to about 10% linolenoyl groups.

10 Claims, No Drawings

NUTRITIONAL FAT SUITABLE FOR ENTERAL AND PARENTERAL PRODUCTS

TECHNICAL FIELD

This application relates to a nutritional fat particularly suitable for enteral and parenteral products.

Fat comprises 40–45% of the calories in the normal American diet, mainly in the form of long-chain triglycerides (LCTs). In addition, fat provides essential fatty acids and serves as a carrier for fat-soluble vitamins. Fat also enhances the flavor and palatability of a given food composition.

Because fat is insoluble in water, its digestion and absorption are complex processes. Before absorption can occur, fat must be emulsified and hydrolyzed to free fatty acids and 2-monoglycerides with the subsequent formation of micelles. Once absorbed into the intestinal cell, the free fatty acids and monoglycerides are then reesterified into triglycerides and phospholipids, formed into chylomicrons and transported to the blood stream via the lymphatic circulation. See Rombeau et al, "Enteral and Tube Feeding," *Clinical Nutrition*, Volume 1, (W. B. Saunders Company, 1984), pp. 178–79.

Disruption at any point in this fat utilization process can result in the maldigestion or malabsorption of the fat. Fat malabsorption can occur as a result of a number of factors. These factors include inadequate absorptive surface area, bile acid or pancreatic insufficiency, inflammatory bowel disease, enteritis, and bacterial overgrowth. Enteral products are often used to combat these fat malabsorption problems. These enteral products have been formulated with LCTs as the fat source. However, fats based on LCTs do not typically provide well-absorbed forms of essential fatty acids, in particular linoleic acid, for those having maldigestion or malabsorption problems.

Enteral products have also been formulated with medium-chain triglycerides (MCTs) as a portion of the fat source. These MCTs provide well-absorbed sources of fat and provide nutritionally beneficial calories. However, MCTs do not supply essential fatty acids such as linoleic acid. Accordingly, it would be desirable to develop a nutritional fat which provides essential fatty acids in a form which is well absorbed by those persons, such as infants, having fat malabsorption problems.

Total parenteral nutrition (TPN) is the method for providing nutrients to those patients who cannot take food orally. TPN is often used to supply nutrients to premature infants. One of the problems with TPN is potential essential fatty acid deficiency (EFAD). EFAD can develop rapidly in children on chronic regiments of fat-free nutrition. Accordingly, a suitable nutritional fat, typically in emulsified form, is desirably included in products used for TPN.

Infused fat particles from such products are cleared from the blood stream in a manner thought to be similar to the clearing of chylomicrons. Following infusion, there is a transient increase in plasma triglycerides. These triglycerides are hydrolyzed to free fatty acids and glycerol by the enzyme, lipoprotein lipase. The free fatty acids either enter the tissues (where they can be oxidized or resynthesized into triglycerides and stored) or circulate in the plasma, bound to albumin. In the liver, the circulating free fatty acids are oxidized and converted to very low density lipoproteins that re-enter the blood stream.

Products used for TPN have typically been formulated with long-chain triglycerides (LCTs) to provide essential fatty acids. However, LCTs' emulsions are not easily cleared from the blood by plasma lipoprotein lipase. Medium-chain triglycerides (MCTs) are cleared rapidly from the blood. However, MCTs, as previously noted, do not supply essential fatty acids such as linoleic acid. Accordingly, it would also be desirable to develop a nutritional fat which provides essential fatty acids in a form which can be rapidly cleared from the blood by those persons on TPN.

BACKGROUND ART

French Pat. No. 2,515,174 to Roussel-UCLAF, published Apr. 29, 1983, discloses triglycerides of formula:

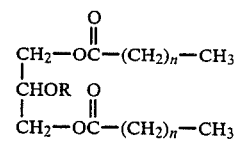

wherein R is an acyl radical of a polyunsaturated fatty acid containing 18 to 22 carbon atoms and n is from 2 to 16. Examples of suitable R groups include those derived from alpha—and gamma—linolenic acid. Preferred values for n include 6 or 10, i.e., octanoyl and dodecanoyl. These triglycerides are useful for supplying polyunsaturated fatty acids in the treatment of fat digestion problems, metabolic disease, etc., and can be formulated in pharmaceutical compositions for oral and parenteral administration.

Babayan, "Medium Chain Length Fatty Acid Esters and Their Medical and Nutritional Applications," *J. Am. Oil Chem. Soc.*, Vol. 58, (1981), pp. 49A–51A, suggests the use of lipids based on medium-chain triglycerides and linoleate in varying ratios for intravenous feeding solutions.

DISCLOSURE OF THE INVENTION

The present application relates to nutritional fats particularly suitable for enteral and parenteral products. These fats consist essentially of from about 50 to 100% by weight triglycerides of the following formula:

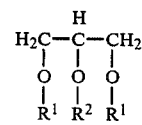

wherein each $R^1$ group is selected from n-heptanoyl, n-octanoyl, n-nonanoyl, n-decanoyl, and n-undecanoyl groups; and the $R^2$ groups comprise from 0 to about 90% saturated acyl groups selected from n-heptanoyl, n-octanoyl, n-nonanoyl, n-decanoyl, n-undecanoyl, lauroyl, myristoyl, palmitoyl, stearoyl and mixtures thereof; from 0 to about 90% oleoyl groups; from about 10 to 100% linoleoyl groups; and from 0 to about 10% linolenoyl groups.

The nutritional fats of the present invention are particularly well absorbed by those patients having fat malabsorption problems. In addition, these nutritional fats provide a source of essential fatty acids. Accordingly, the nutritional fats of the present invention are particularly suitable for enterally administrable compositions which further comprise a source of carbohydrates and amino acids, as well as other optional components typically present in enteral products.

In addition, the nutritional fats of the present invention are hydrolyzed by plasma lipoprotein lipase so that they can be rapidly cleared from the blood. Since these nutritional fats also provide a source of essential fatty acids, they are particularly suitable for parenterally administrable compositions used in total parenteral nutrition (TPN).

A. Definitions

As used herein, the term "comprising" means various compatible components can be conjointly employed in the enterally or parenterally administrable compositions of the present invention. Accordingly, the term "comprising" encompasses the more restrictive terms "consisting essentially of" and "consisting of".

As used herein, the term "nutritionally effective amount" refers to an amount of a particular component of the enterally or parenterally administrable composition sufficient to provide a nutritional benefit to the individual taking it.

B. Nutritional Fat

The key to the nutritional fat of the present invention are triglycerides of the following formula:

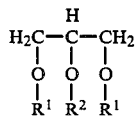

Each $R^1$ group is a linear $C_7$–$C_{11}$ saturated acyl group, i.e., n-heptanoyl, n-octanoyl, n-nonanoyl, n-decanoyl, and n-undecanoyl. Preferably, each $R^1$ group is an n-octanoyl group, i.e., a 1,3-dioctanoyl triglyceride.

The $R^2$ groups of these triglycerides comprise from 0 to about 90% saturated acyl groups selected from n-heptanoyl, n-octanoyl, n-nonanoyl, n-decanoyl, n-undecanoyl, lauroyl, myristoyl, palmitoyl, stearoyl and mixtures thereof; from 0 to about 90% oleoyl groups; from about 10 to 100% linoleoyl groups; and from 0 to about 10% linolenoyl groups. Preferably, the $R^2$ groups comprise from about 10 to about 20% saturated acyl groups; from about 10 to about 30% oleoyl groups; from about 50 to about 80% linoleoyl groups; and from 0 to about 6% linolenoyl groups.

The nutritional fat consists essentially of from about 50 to 100% by weight of these desired triglycerides. The remaining triglycerides present in the nutritional fat are typically other reaction products obtained during synthesis of the desired triglycerides. However, the nutritional fat can also comprise blends of the desired triglycerides with other triglycerides obtained from fat sources such as vegetable oils. Preferably, the nutritional fat consists essentially of from about 90 to 100% by weight of these desired triglycerides.

The desired triglycerides which form the nutritional fat can be prepared by base or acid catalyzed esterification of the appropriate 1,3-diglycerides with a fatty acid, fatty acid anhydride, or fatty acid chloride. The 1,3-diglycerides can be prepared by reaction of the appropriate fatty acids, or preferably their methyl esters, with glycerol. The triglycerides are preferably prepared by esterifying the 1,3-diglycerides with mixtures of the fatty acids, anhydrides or acid chlorides. Suitable fatty acid mixtures can be derived from the appropriate vegetable oils. Particularly preferred vegetable oils for forming these fatty acid mixtures include soybean oil, corn oil, sunflower oil, safflower oil, and mixtures thereof. Esterification of the 1,3-diglycerides can be made more selective by using the catalysts disclosed in U.S. Pat. No. 3,410,881 to Martin et al., issued Nov. 12, 1968, or U.S. Pat. No. 28,737 to Yetter, reissued Mar. 16, 1976, which are incorporated by reference.

The synthesis of 2-linoleoyl-1,3-dioctanoin according to the present invention is described as follows:

1,3-dioctanoin was prepared by reacting 2.2 moles of octanoic acid with 1 mole of glycerol in toluene using 1% p-toluene sulfonic acid as the catalyst. This mixture was refluxed and $H_2O$ was removed in a trap. The mixture was then cooled and washed with $H_2O$. The excess octanoic acid was removed by distillation under a vacuum at 100° to 150° C. The residue was dissolved in 6 volumes of hexane, crystallized at 0° C. and then recrystallized from hexane at 0° C.

The 1,3-dioctanoin (13 g.) is acylated with a 20% excess of linoleoyl chloride. The crude product obtained is diluted with ether and then is washed successively with $H_2O$, dilute HCl, and $H_2O$. The solvent is evaporated and the remaining oil is stirred for 1 hour with boiling $H_2O$ to hydrolyze any anhydrides present. The boiled product is cooled, dissolved in petroleum ether/ether (1:1 ratio) solvent and refined with aqueous alcoholic $K_2CO_3$ to remove fatty acids. The refined product is dried with $Na_2SO_4$, filtered and then the solvent is evaporated.

Portions (2.5 ml.) of the filtered product are purified by silica gel chromatography. The column is eluted with 175 ml. of 1% ether/petroleum ether solvent to remove non-polar materials and then with 150 ml. of 10% ether/petroleum ether to elute the desired triglyceride. Kiesel-gel 60 (25 g.) is used as the absorbent. The triglyceride fractions are combined, concentrated and dried under a vacuum.

The synthesis of mixed 1,3-dioctanoyl triglycerides according to the present invention is described as follows:

The methyl ester of octanoic acid (2.2 moles), glycerol (1 mole) and sodium methoxide (0.5% by weight of the methyl ester) are reacted together at 100° to 120° C. and a pressure of 30 to 50 mm Hg. for 1 to 2 hours. This reaction mixture is cooled, 0.2% more sodium methoxide is added and then the mixture is stored for 1 to 3 days at 4° C. Sufficient acetic acid to neutralize the remaining sodium methoxide is then mixed into the paste-like mixture. This paste is warmed slowly, water washed, and dried under vacuum at no more than 60° C. The crude mixture containing 1,3-dioctanoin is then esterified with soybean oil fatty acid anhydrides according to the method disclosed in U.S. Pat. No. 3,410,881. The crude mixture of triglycerides is then washed and deodorized to remove excess fatty acids.

C. Enterally administrable compositions

The nutritional fats of the present invention are especially suitable for inclusion in enterally administrable compositions. See Rombeau et al, "Enteral and Tube Feeding," *Clinical Nutrition*, Volume 1, (W. B. Saunders Co., 1984), pages 171–96 (incorporated by reference), which provides a general description of enteral products and their formulation. Basically, enterally administrable compositions of the present invention comprise the following components:
(1) the nutritional fat of the present invention;
(2) a source of carbohydrates;
(3) a source of amino acids; and
(4) optional components such as vitamins and minerals.
The composition can be formulated as a dry mixture or else mixed with water to provide a fluid formulation.

The nutritional fat of the present invention is included in the enteral composition in a nutritionally effective amount. The particular amount of fat included in the composition typically depends upon the nutritional fat used, as well as the nutritional benefits desired. Usually, the nutritional fat is included in an amount of from about 0.2 to about 10% by weight (from about 2 to about 100 g. per 1000 ml. for fluid formulations) of the composition. Preferably, the nutritional fat is included in an amount of from about 2 to about 10% by weight (from about 20 to about 100 g. per 1000 ml.)

Enterally administrable compositions of the present invention further comprise a nutritionally effective amount of a source of carbohydrates. The particular amount of the carbohydrate source included typically depends upon the source used, as well as the nutritional benefits desired. Usually, the carbohydrate source is included in an amount of from about 10 to about 37% by weight (from about 100 to about 370 g. per 1000 ml.) of the composition. Preferably, the carbohydrate source is included in an amount of from about 12 to about 25% by weight (from about 120 to 250 g. per 1000 ml.).

Various carbohydrate sources can be used in enteral products of the present invention. For example, suitable sources of carbohydrates include polysaccharides/oligosaccharides such as starch, glucose polymers, and maltodextrins; disaccharides such as lactose, sucrose, dexrins, and maltose; and monosaccharides, such as glucose. Glucose is a particularly preferred source of carbohydrates. See Rombeau et al, supra at pages 172-74.

Enterally administrable compositions of the present invention further comprise a nutritionally effective amount of a source of amino acids. The particular amount of the amino acid source included typically depends upon the source used, as well as the nutritional benefits desired. Usually, the amino acid source is included in an amount of from about 1.5 to about 7.5% by weight (from about 15 to about 75 g. per 1000 ml.) of the composition. Preferably, the amino acid source is included in an amount of from about 2 to about 7% by weight (from about 20 to about 70 g. per 1000 ml.).

The amino acids included in enteral products of the present invention can be derived from a variety of different sources. For example, suitable sources of amino acids include intact proteins, proteins partially hydrolyzed into smaller polypeptide fragments (oligopeptides, dipeptides and tripeptides) or crystalline L-amino acids. Amino acid sources are typically selected to provide the essential amino acids needed in the human diet. The essential amino acids include histidine, isoleucine, leucine, lysine, methionine and cystine, phenylalanine and tyrosine, threonine, tryptophan, and valine. See Rombeau et al, supra at pages 174-78. Suitable sources of amino acids are also disclosed in U.S. Pat. No. 3,697,287 to Winitz, issued Oct. 10, 1972; 3,698,912, to Winitz, issued Oct. 17, 1972; and U.S. Pat. No. 3,701,666 to Winitz; issued Oct. 31, 1972, all of which are incorporated by reference.

Other optional ingredients typically found in enteral products can also be included. For example, vitamins and other minerals can be included in the enteral products of the present invention. Suitable vitamins include A, D, E, C, $B_1$, $B_2$, $B_6$, $B_{12}$, folic acid, niacin, thiamine, and riboflavin. Minerals which can be included in the enteral product include calcium, iron, zinc, potassium, magnesium, maganese, copper, phosphorus, and the like.

The enterally administrable compositions of the present invention are formulated to provide the appropriate osmolality. Osmolality is a function of the number and size of molecular and ionic particles present in a given volume. These particles include electrolytes, minerals, carbohydrates, and proteins or amino acids. The osmolality of enteral products of the present invention is typically in the range of from about 300 to about 900 mOsm/l. Preferably, the osmolality is in the range from about 300 to about 650 mOsm/l.

An enteral product (fluid formulation) according to the present invention can be formulated as follows:

| Ingredient | Amount (per 1000 ml.) |
| --- | --- |
| Vit. A | 2778 IU |
| Vit. D | 222 IU |
| Vit. E | 16.7 IU |
| Vit. K | 37 microg. |
| Vit. C | 33 mg. |
| Folic Acid | 0.22 mg. |
| Thiamine | 0.83 mg. |
| Riboflavin | 0.94 mg. |
| $B_6$ | 1.1 mg. |
| $B_{12}$ | 3.3 microg. |
| Niacin | 11.1 mg. |
| Choline | 41 mg. |
| Biotin | 0.17 mg. |
| Pantothenic Acid | 5.6 mg. |
| Sodium | 20.4 mEq. |
| Potassium | 30 mEq. |
| Chloride | 20.4 mEq. |
| Calcium | 0.56 g. |
| Phosphorus | 0.56 g. |
| Magnesium | 222 mg. |
| Iodide | 83 microg. |
| Manganese | 1.6 mg. |
| Copper | 1.1 mg. |
| Zinc | 8.3 mg. |
| Iron | 10 mg. |
| Carbohydrate | 200 g. |
| Protein | 21 g. |
| Nutritional Fat of present invention | 25 g. |

D. Parenterally administrable compositions

The nutritional fats of the present invention are also especially suitable for inclusion in parenterally administrable compositions for TPN. Basically, parenterally administrable compositions of the present invention comprise the following components:
(1) an aqueous phase (usually pyrogen-free distilled water);
(2) the nutritional fat of the present invention dispersed in the aqueous phase;
(3) if needed, a suitable emulsifier to disperse the nutritional fat in the aqueous phase; and
(4) optional components such as vitamins and minerals.

The nutritional fat of the present invention is included in the parenteral composition in a nutritionally effective amount. The particular amount of fat included typically depends upon the nutritional fat used, as well as the nutritional benefits desired. Usually, the nutritional fat is included in an amount of from about 0.2 to about 20% by weight (from about 2 to about 200 g. per 1000 ml.) of the parenteral composition. Preferably, the nutritional fat is included in an amount of from about 2 to about 10% by weight (from about 20 to about 100 g. per 1000 ml.).

Parenteral products of the present invention typically include an emulsifier to disperse the nutritional fat in the aqueous phase. Suitable emulsifiers (oil-in-water) include lecithin and polyoxyethylene sorbitan monoesters such as TWEEN 60 and TWEEN 80. Other suitable oil-in-water emulsifiers can also be used. The emulsifier is used in an amount effective to disperse the nutritional fat in the aqueous phase. Typically, the emulsifier is included in an amount of from about 0.5 to about 1.5% by weight (from about 5 to about 15 g. per 1000 ml.) of the composition, preferably in an amount from about 1 to about 1.3% by weight (from about 10 to about 13 g. per 1000 ml.). Glycerol is also typically included at from about 10 to about 30% by weight of the nutritional fat to aid in its dispersion.

Other optional ingredients typically found in products for parenteral nutrition can also be included. For example, carbohydrates, amino acids, vitamins and minerals can be included in the parenteral products of the present invention. A preferred carbohydrate source is glucose. A suitable amino acid source is a mixture of crystalline L-amino acids. Suitable vitamins include A, D, E, C, $B_1$, $B_2$, $B_6$, $B_{12}$, folic acid, niacin, thiamine and riboflavin. Minerals which can be included in the parenteral product include calcium, iron, zinc, potassium, magnesium, maganese, copper, phosphorus, and the like.

The parenterally administrable compositions of the present invention are formulated to provide the appropriate osmolality. The osmolality of parenteral products of the present invention is typically in the range of from about 300 to about 900 mOsm/l. Preferably, the osmolality is in the range from about 300 to about 650 mOsm/l. Also, the pH of the parenteral composition is appropriately adjusted, typically to about 5.5 to about 9 by using sodium hydroxide.

A parenteral product according to the present invention can be formulated as follows:

| Ingredient | Amount (per 1000 ml.) |
| --- | --- |
| Vit. A | 2778 IU |
| Vit. D | 222 IU |
| Vit. E | 16.7 IU |
| Vit. K | 37 microg. |
| Vit. C | 33 mg. |
| Folic Acid | 0.22 mg. |
| Thiamine | 0.83 mg. |
| Riboflavin | 0.94 mg. |
| $B_6$ | 1.1 mg. |
| $B_{12}$ | 3.3 microg. |
| Niacin | 11.1 mg. |
| Choline | 41 mg. |
| Biotin | 0.17 mg. |
| Pantothenic Acid | 5.6 mg. |
| Sodium | 20.4 mEq. |
| Potassium | 30 mEq. |
| Chloride | 20.4 mEq. |
| Calcium | 0.56 g. |
| Phosphorus | 0.56 g. |
| Magnesium | 222 mg. |
| Iodide | 83 microg. |

-continued

| Ingredient | Amount (per 1000 ml.) |
| --- | --- |
| Manganese | 1.6 mg. |
| Copper | 1.1 mg. |
| Zinc | 8.3 mg. |
| Iron | 10 mg. |
| Lecithin | 10 g. |
| Nutritional Fat of present invention | 25 g. |
| Glycerol | 2.25 g. |
| Water | balance |

What is claimed is:

1. A nutritional fat which consists essentially of from about 50 to 100% by weight of a triglyceride component comprising one or more compounds of the following formula:

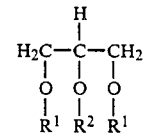

wherein $R^1$ is n-octanoyl; and the $R^2$ groups in the trigylceride component comprise from 0 to about 90% saturated acyl groups selected from the group consisting of n-heptanoyl, n-octanoyl, n-nonanoyl, n-decanoyl, n-undecanoyl, lauroyl, myristoyl, palmitoyl, stearoyl, and mixtures thereof; from 0 to about 90% oleoyl groups; from about 10 to 100% linoleoyl groups; and from 0 to about 10% linolenoyl groups.

2. The nutritional fat of claim 1, wherein the $R^2$ groups of said triglyceride component comprise from about 10 to about 20% saturated acyl groups; from about 10 to about 30% oleoyl groups; from about 50 to about 80% linoleoyl groups; and from 0 to about 6% linolenoyl groups.

3. The nutritional fat of claim 1, which consists essentially of from about 90 to 100% by weight of said triglyceride component.

4. An enterally administerable composition, which comprises:
(a) a nutritionally effective amount of the nutritional fat of claim 1;
(b) a nutritionally effective amount of a source of carbohydrates; and
(c) a nutritionally effective amount of a source of amino acids.

5. The composition of claim 4, which comprises from about 0.2 to about 10% by weight of said nutritional fat.

6. The composition of claim 5, wherein said nutritional fat consists essentially of from about 90 to 100% by weight of said triglyceride component.

7. The composition of claim 6 wherein the $R^2$ groups of said triglyceride component comprise from about 10 to about 20% saturated acyl groups; from about 10 to about 30% oleoyl groups; from about 50 to about 80% linoleoyl groups; and from 0 to about 6% linolenoyl groups.

8. The composition of claim 7, which comprises from about 10 to about 37% by weight of said carbohydrate source and from about 1.5 to about 7.5% by weight of said amino acid source.

9. The composition of claim 8, wherein said carbohydrate source comprises glucose.

10. The composition of claim 9, which is in fluid form.

* * * * *

UNITED STATES PATENT AND TRADEMARK OFFICE
CERTIFICATE OF CORRECTION

PATENT NO. : 4,753,963
DATED : June 28, 1988
INVENTOR(S) : Robert A. Volpenhein

It is certified that error appears in the above-identified patent and that said Letters Patent are hereby corrected as shown below:

Cover Sheet: [75] Inventors: "Ronald J. Jandacek, Cincinnati, Ohio; Robert A. Volpenhein, West Harrison, Ind."

Should be --Robert A. Volpenhein, West Harrison, Ind.--

Signed and Sealed this

Twenty-eighth Day of March, 1989

Attest:

DONALD J. QUIGG

*Attesting Officer*  *Commissioner of Patents and Trademarks*